US00PP23998P2

(12) United States Plant Patent
Werner et al.

(10) Patent No.: US PP23,998 P2
(45) Date of Patent: Oct. 22, 2013

(54) ***CERCIS* TREE NAMED 'WHITEWATER'**

(50) Latin Name: *Cercis canadensis*
Varietal Denomination: WHITEWATER

(75) Inventors: Dennis James Werner, Raleigh, NC (US); Layne Karlton Snelling, Cary, NC (US)

(73) Assignee: North Carolina State University, Raleigh, NC (US)

( * ) Notice: Subject to any disclaimer, the term of this patent is extended or adjusted under 35 U.S.C. 154(b) by 770 days.

(21) Appl. No.: 12/658,499

(22) Filed: Feb. 9, 2010

Related U.S. Application Data

(60) Provisional application No. 61/207,615, filed on Feb. 17, 2009.

(51) Int. Cl.
*A01H 5/00* (2006.01)

(52) U.S. Cl.
USPC ..... Plt./216

(58) Field of Classification Search
USPC ..... Plt./216
See application file for complete search history.

*Primary Examiner* — Kent L Bell

(57) ABSTRACT

*Cercis* 'Whitewater' is a new and distinct variety of redbud that has the following unique combination of desirable features that are outstanding in a new variety.

1. Weeping growth habit.
2. Ease of asexual propagation using chip-budding.
3. Foliage with green and white variegation.

3 Drawing Sheets

Genus and species: Genus: *Cercis* (Leguminosae). Species: *canadensis* (eastern redbud).

Cultivar denomination: The inventive cultivar of *Cercis canadensis* disclosed herein has been given the cultivar denomination 'WHITEWATER'.

BACKGROUND OF THE INVENTION

The present invention relates to a new and distinct cultivar of *Cercis canadensis* (redbud) grown as an ornamental tree for home and commercial landscapes. Redbud is typically grown as a small tree for its attractive purple flowers that are borne in the spring, and sometimes for its interesting foliage color (purple, variegated, or golden leaf forms) or architectural form.

The new and distinct cultivar of redbud resulted from a formal breeding program established by the inventors in Raleigh, N.C., United States. One of the objectives of the breeding program was to develop a variegated-leaf form of redbud that exhibited the weeping growth habit. 'WHITEWATER' originated as a second-generation descendant from a controlled hybridization of *Cercis canadensis* cultivars 'Silver Cloud' and 'Covey' made in spring 1999 in Raleigh, N.C. Established trees of both cultivars growing in a botanical garden in Raleigh, N.C. were used to make the controlled hybridizations. The hybridizations were made in both directions, with each cultivar being used as both a seed and pollen parent. Fruit pods and seed were obtained on both the 'Covey' and 'Silver Cloud' trees. 'Covey' (U.S. Plant Pat. No. 10,328) was introduced in Madison, Ohio in 1997 and is described as a green leafed, weeping form of *Cercis canadensis* with light purple flowers. 'Silver Cloud' (non-patented) is a non-weeping, variegated-leaf form of eastern redbud (*Cercis canadensis*) introduced in 1964 in Crestwood, Ky. Both cultivars are commonly available in commerce.

The first generation seeds resulting from the spring 1999 hybridization were harvested in fall of 1999 and germinated in a greenhouse in Raleigh, N.C. in the winter of 2000. Three seedlings, designated NC99-18-1, NC99-18-2, NC99-18-3, were obtained from the 'Covey' seed parent, and one seedling, designated NC99-18-4, was obtained from the 'Silver Cloud' seed parent. These resulting 4 first generation seedlings were grown in a greenhouse in year 2000, and subsequently planted together in a field setting at a research station, isolated from other redbuds, in spring 2001. All four of these first generation seedlings (NC99-18-1, NC99-18-2, NC99-18-3, and NC99-18-4) showed green leaves and normal (non-weeping) growth habit. These trees flowered and set fruit in spring 2005, and the second generation seed was collected and bulked that same year off of all 4 trees. This bulked seed was germinated in a greenhouse in Raleigh, N.C. in December, 2005. From these approximately 1600 seedlings, 102 seedlings showing green and white variegated leaves and weeping growth habit were selected and grown in the greenhouse in spring and summer, 2006. These 102 seedlings were later transplanted to the field in November, 2006, and one tree, later designated 'WHITEWATER', was selected in summer 2007 as the best individual for its green and white variegated leaf color and weeping growth habit. This original tree demonstrated characteristics identical to those subsequently expressed on other trees when propagated by chip budding. This single tree is the subject of the present invention 'WHITEWATER'.

The distinguishing traits of 'WHITEWATER' are its distinctive green and white variegated leaves, and its weeping growth habit. The cultural requirements for 'WHITEWATER' are well-drained soil, full sun to partial shade, and moderate moisture. 'WHITEWATER' exhibits no serious pest or disease problems known to the inventors.

The closest comparisons known to the inventors are its grandparents, 'Silver Cloud' and 'Covey'. In direct comparisons of 'WHITEWATER' with the 2 grandparent cultivars in the inventor's experimental trials, trees of 'WHITEWATER' are weeping in growth, compared to the non-weeping growth of 'Silver Cloud'. 'WHITEWATER' differs from the 'Covey' grandparent in having variegated leaves. 'WHITEWATER' is clearly distinct from its original grandparents. Two other weeping architecture redbuds currently in the trade, 'Traveller' (U.S. Plant Pat. No. 8,640) and 'Cascading Hearts' (U.S. Plant Pat. No. 18,528), have entirely green leaves, unlike the variegated leaves of 'WHITEWATER'. 'WHITEWATER' differs from its parents (NC99-18-1, NC99-18-2, NC99-18-3, and NC99-18-4). Because seed were bulked from all 4 first-generation trees, it is impossible to say with certainty which specific parental selection 'WHITEWATER' was actually derived from. However, all 4 parental selections showed entirely green leaves and non-weeping architecture, distinctly different from 'WHITEWATER', which shows variegated leaves and weeping growth habit.

The first asexual propagation of 'WHITEWATER' was conducted by Alex and Harald Neubauer on behalf of the inventors in fall 2007 in Belvidere, Tenn. 'WHITEWATER' has subsequently been propagated in the same location in 2008. In all cases, the original tree was propagated asexually by chip budding in late summer onto *Cercis canadensis* rootstock. Such budded trees heal rapidly, and resume normal growth the following spring after budding. Two trees derived from chip budding of the cultivar were established in the inventor's test plots in January 2009. During all asexual propagation, the characteristics of the original tree have been maintained. Trees derived from chip budding exhibit characteristics identical to those of the original tree, and no aberrant phenotypes have appeared.

Performance evaluation of the original tree and budded trees demonstrate this cultivar to be relatively consistent in its characteristics even under the different growing conditions associated with yearly climatic variation.

Trees of the new cultivar are moderately vigorous after chip budding in the nursery setting, growing up to 1.2 meters the following growing season after fall budding. Trees are weeping in growth habit. 'WHITEWATER' produces light purple flowers in early spring.

'WHITEWATER' is distinguished from other related known cultivars based on the unique combination of traits including weeping growth habit and green and white variegated leaf color.

The new cultivar has been named the 'WHITEWATER' cultivar. No public sale of 'WHITEWATER' has yet taken place at the time of this application.

SUMMARY OF THE INVENTION

'WHITEWATER' is a new and distinct cultivar of redbud tree that has the following unique combination of desirable features outstanding in a new cultivar. In combination these traits set 'WHITEWATER' apart from all other existing cultivars of redbud known to the inventors.

1. 'WHITEWATER' has weeping growth habit.
2. 'WHITEWATER' is asexually propagated using chip budding.
3. 'WHITEWATER' has large, attractive green and white variegated leaves.

BRIEF DESCRIPTION OF THE DRAWINGS

The photographs in the drawings were made using digital photography techniques, and show the colors as true as reasonably possible by digital photography. Photographs for FIGS. 1 and 2 were taken from the original two-year-old tree growing in the inventor's research plot in Raleigh, N.C. The photograph for FIG. 3 was taken from the same tree, but at 4 years of age.

DETAILED BOTANICAL DESCRIPTION OF THE VARIETY

Figure 1:
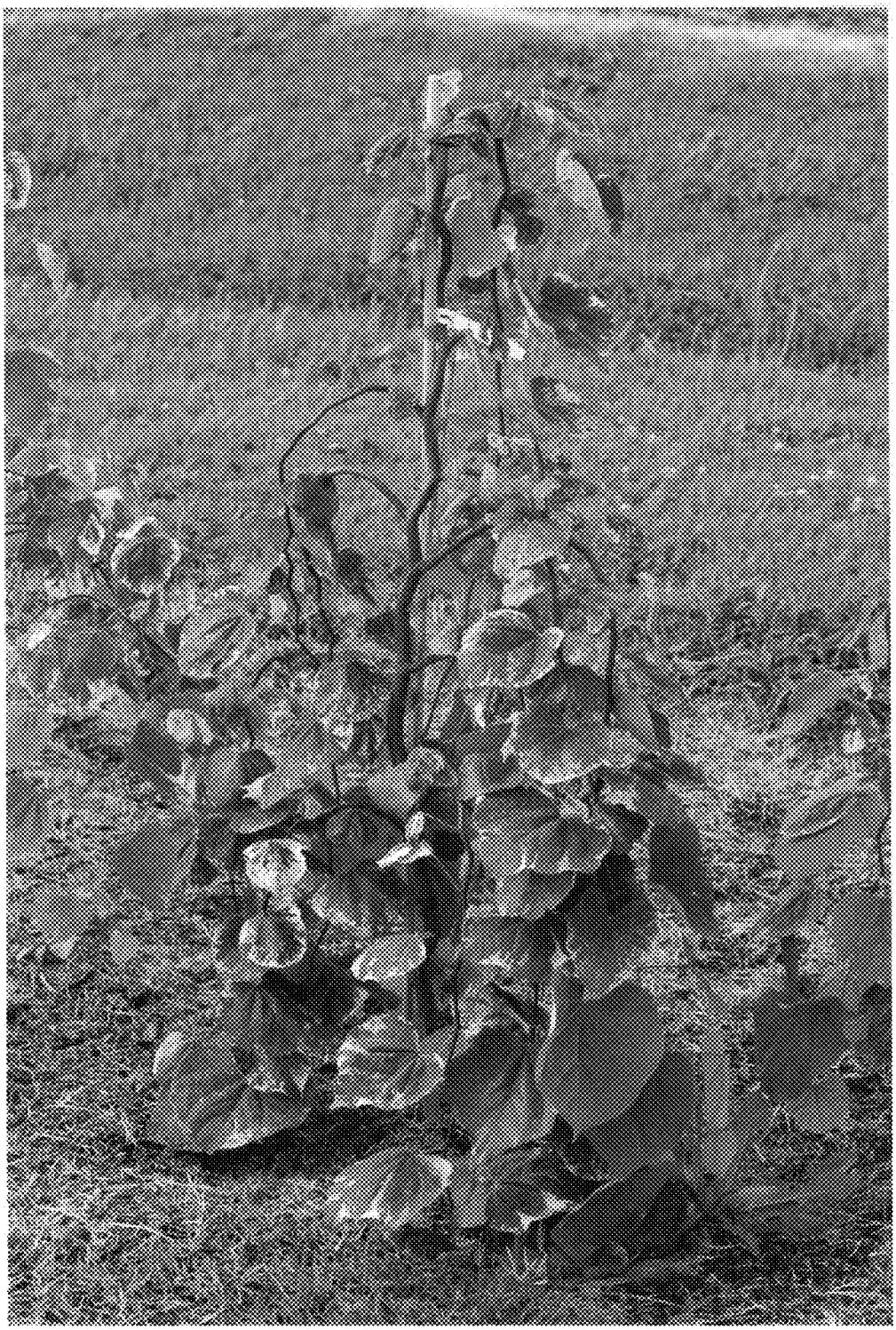
FIG. 1 shows a typical tree of 'WHITEWATER', showing the weeping habit and variegated leaves.
Figure 2:
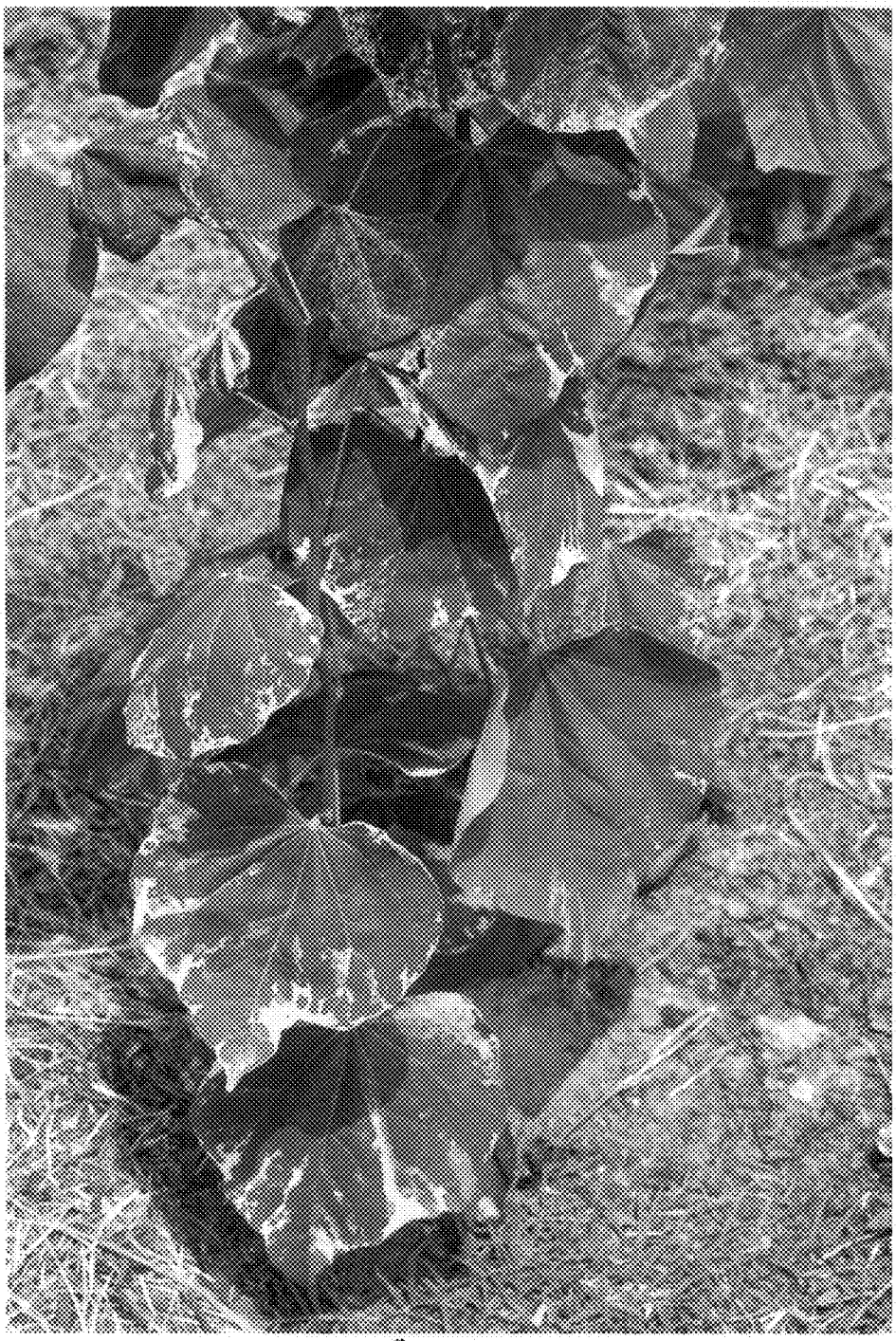
FIG. 2 shows the typical variegation coloration and form of leaves of 'WHITEWATER'. This figure shows both recently formed and older leaves.
Figure 3:
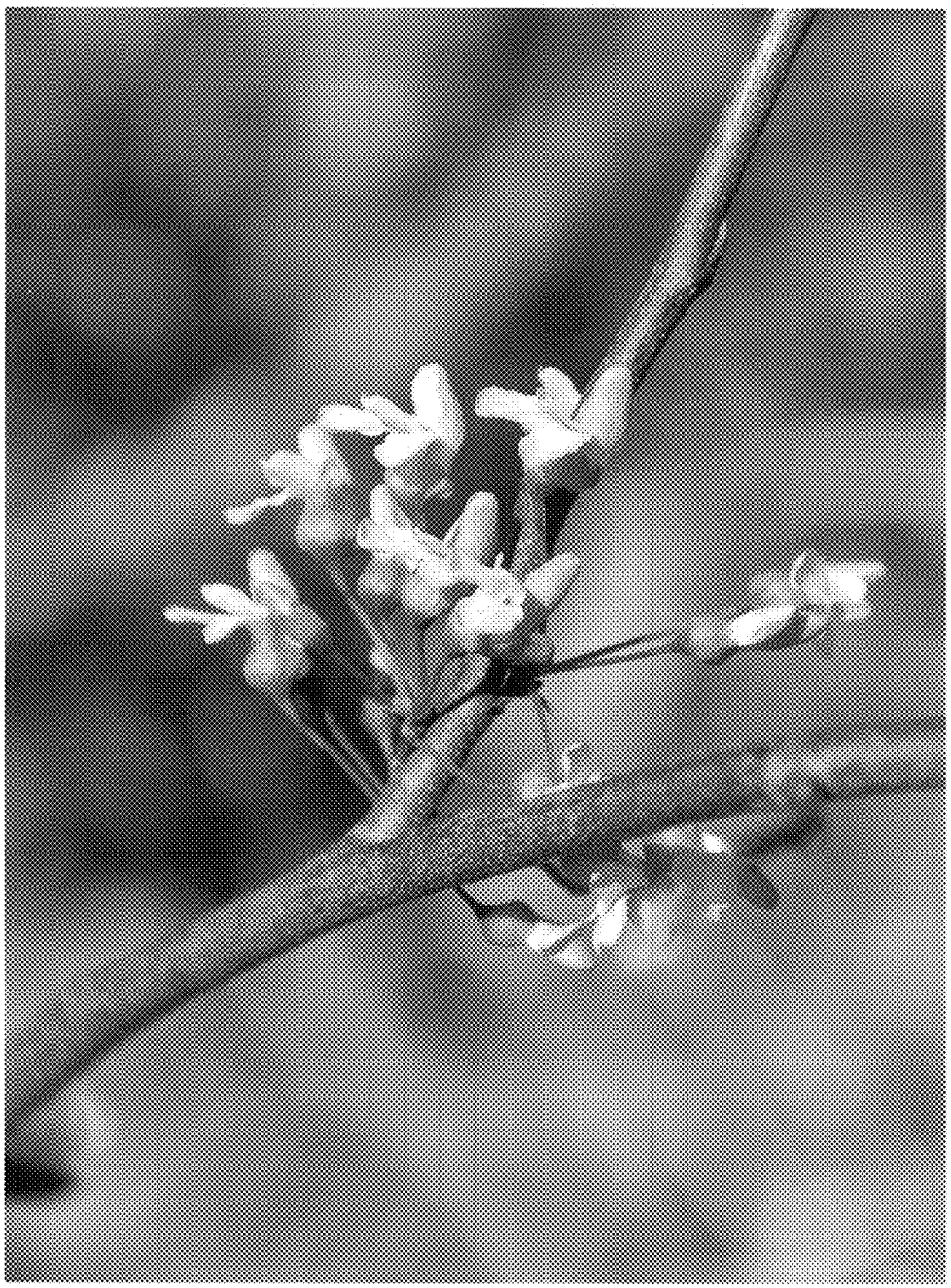
FIG. 3 shows the typical form and coloration of flowers on 'WHITEWATER'.

The following is a detailed description of the botanical and ornamental characteristics of the subject redbud 'WHITEWATER'. Color data are based on The Royal Horticultural Society Colour Chart, The Royal Horticultural Society, London, 5$^{th}$ edition, 2007. Where dimensions, sizes, colors and other characteristics are given, it is to be understood that such characteristics are approximations of averages set forth as accurately as practicable.

The descriptions reported herein are from the original three-year-old tree growing at the research station in Raleigh, N.C.

Genus: *Cercis*.

Species: *canadensis*.

Denomination: 'WHITEWATER'.

Commercial classification: Tree, deciduous.

Common name: Redbud.

Type: Ornamental.

Uses: Small landscape tree for residential and commercial landscapes.

Cultural requirements: Full sun to partial shade exposure, well-drained soil, and moderate moisture.

Parentage: Second generation selection derived from the hybridization of *Cercis canadensis* (eastern redbud) 'Covey' and *Cercis canadensis* 'Silver Cloud'. 'Covey' and 'Silver Cloud' are grandparents. Selections NC99-18-1, NC99-18-2, NC99-18-3, and NC99-18-4, all derived from hybridization of 'Covey' and 'Silver Cloud', are the immediate parents of 'WHITEWATER'.

Plant description:

*Blooming period*.—Early spring in Raleigh, N.C.

*Blooming habit*.—Flowers produced both on one-year-old wood, and on older wood (cauliflory).

*Vigor*.—Moderate vigor.

*Plant habit*.—Weeping, well-branched.

*Height and spread*.—Height dictated by nursery management and cultural practices. Can be trained as a ground cover, or a small weeping tree typically up to six feet in height. Spread generally 2-3 feet. Tree currently described is 1.27 m height, and 0.92 m width.

*Hardiness*.—To date, hardy to negative 12.8 degrees Centigrade. Not tested below this temperature. Anticipated adapted from USDA hardiness zones 6-9.

*Propagation*.—Chip-budding onto seedling rootstock, typically in late summer in the southeastern U.S.

*Root system*.—Fibrous.

*Seasonal interest*.—Large, green and white variegated leaves on a weeping tree. Attractive purple flowers in early spring.

*Disease and pest susceptibility and resistance*.—No particular susceptibility or resistance.

*Special growing requirements*.—None. Best grown in full sun to partial shade in moderately well drained soil.

Trunk:

*Dimensions.*—4.5 cm diameter measured 0.15 m above soil line.

*Bark surface.*—Slightly rugose.

*Color.*—Lighter sectors=blue-green (122D). Darker sectors=grayed-green (188A).

Stems:

*Shape.*—Stem cross section is circular.

*Length.*—Average 0.4 m of new growth yearly.

*Color.*—Yellow-green (N77A) on newly formed growth. Yellow-green (144A) on dormant one-year-old shoots. Brown (N200A) on two-year-old stems.

*Diameter.*—3-4 mm near base of stem on mature one-year-old stems.

*Stem surface.*—Glaucous.

*Pubescence.*—Lacking.

*Internode length.*—Variable. 2.1 to 6.4 cm, averaging 3.4 cm between nodes.

*Lenticels.*—Numerous, tiny (1 mm or less). Color (N200B), measured in early spring. Circular.

Foliage:

*Type.*—Deciduous.

*Leaf arrangement.*—Alternate.

*Leaf division.*—Simple.

*Leaf shape.*—Broad-ovate to deltoid.

*Leaf base.*—Cordate.

*Leaf apex.*—Obtuse to acute.

*Leaf venation.*—Reticulate.

*Leaf surface (abaxial and adaxial).*—Glaucous.

*Leaf margin.*—Entire.

*Leaf attachment.*—Petiolate.

*Petiole dimensions.*—5.0 cm length. 2.0 mm width at base tapering to 1.0 mm at apex (nearest to leaf blade).

*Petiole shape.*—Round.

*Petiole color.*—Yellow-green (148A) on mature leaf.

*Petiole surface.*—Smooth, lacking pubescence.

*Leaf color (immature leaf).*—Adaxial (upper) surface. White sector=white (NN155D). Green sector=green (128B). Abaxial (lower) surface. White sector=white (NN155D). Green sector=green (128B).

*Leaf color (mature leaf).*—Adaxial surface. Green sector=green (139A), white sector=white (150D). Abaxial surface. Green sector=greyed-green (191A), white sector=green-white (157A).

*Leaf color (mature entire green leaf).*—Adaxial surface. Green (139A). Abaxial surface. Greyed-green (191A).

*Vein color (abaxial surface).*—Yellow-green (146D).

*Leaf length.*—Average length (10 leaves)=10.5 cm from leaf tip to base of midvein/apex of petiole. 11.5 cm from leaf tip to base of leaf blade.

*Leaf width.*—Average width (10 leaves)=11.5 cm.

*Foliar fragrance.*—None detectable.

*Stipules.*—None present.

*Causes for variation in color.*—Green and white leaf variegation is maximal under normal sunlight and cool temperatures. Under normal sunlight to partial shade, new foliage emerges with green and white variegation, with variegation becoming less pronounced (white sector begins to show some expression of green pigment) as an individual leaf matures later in the growing season (late summer). Variegated expression diminishes in deep shade and under heat stress.

Flowers:

*Inflorescence.*—Papillonaceous flowers arranged in a small cluster.

*Number of flowers per cluster.*—2 to 8.

*Arrangement.*—Sessile clusters.

*Location.*—Nodes of previous years growth, and along older stems and occasionally the trunk (cauliflory).

*Length of bloom.*—2-3 weeks, depending on weather conditions.

*Flower length.*—1.0 cm from base of calyx to tip of keel.

*Flower width.*—3 mm immediately prior to anthesis.

*Flower depth.*—5 mm.

*Pedicel length.*—1.4 cm.

*Pedicel diameter.*—0.5 mm.

*Pedicel shape.*—Round.

*Pedicel color.*—Purple group (71A).

*Pedicel surface.*—Smooth.

*Flowers persistent or self-cleaning.*—Self-cleansing.

*Flower fragrance.*—Lacking.

*Lastingness of the overall inflorescence.*—2-3 weeks.

*Lastingness of an individual flower.*—5-7 days.

Flower bud:

*Shape.*—Broadly oval.

*Color.*—Purple group (N77A).

*Surface.*—Smooth.

*Diameter.*—1.0 to 1.5 mm.

*Length.*—3 to 4 mm.

Petals:

*Number.*—5, lower 2 fused to form keel.

*Petals fused or unfused.*—3 unfused, 2 fused.

*Standard (banner) color.*—Tip=Purple (N78C). Base=Purple (62D).

*Keel petal color.*—Tip=Purple (N78B). Base=Purple (62D).

*Wing petal color.*—Tip=Purple (N78B). Base=Purple (62D).

*Petal surface (adaxial).*—Smooth

*Petal surface (abaxial).*—Smooth.

*Petal margin.*—Entire.

Calyx:

*Shape.*—Vase-shaped.

*Length.*—5 mm.

*Diameter.*—6 mm.

*Color (outer surface).*—Purple (71B).

*Color (inner surface).*—Purple (71B).

*Surface (inner).*—Smooth.

*Surface (outer).*—Smooth.

Sepals:

*Number.*—1 — fused.

*Color (adaxial surface).*—Purple (71B).

*Color (abaxial surface).*—Purple (71B).

*Surface (adaxial surface).*—Smooth.

*Surface (abaxial surface).*—Smooth.

Reproductive organs:

*Pistil.*—Dimensions: 9.0 mm length. 1 mm width. Color: Red-purple (59B). Surface: Smooth.

*Stigma.*—Shape: Round. Length: Less than 1 mm. Width: Less than 1 mm. Color: Red-purple (59B).

*Style.*—Shape: Narrow, cylindrical. Length: Less than 1 mm. Width: Less than 1 mm. Color: Red-purple (60D).

*Stamens.*—Number: 10. Fused or unfused at base: 9 fused at base. 1 free. Length: 7 mm. Width: Less than 1 mm. Color (filament): Red-purple (59B).

*Anthers*.—Shape: Round to slightly oblong. Length: Less than 1 mm. Width: Less than 1 mm. Color: Red-purple (59B). Immediately prior to anthesis.

*Pollen*.—Color: Yellow group (9B). Amount: Abundant.

*Ovary*.—Position: Superior. Shape: Elongate. Length: 2 mm. Width: 1.0 mm at base, tapering to less than 1 mm at top. Color: Red-purple (59B).

*Fruit*.—No fruit or seed produced to date. Lack of pod production likely due to the young age of the plant.

That which is claimed is:

1. A new and distinct variety of redbud tree (*Cercis*) substantially as illustrated and described, characterized by its weeping growth habit, and attractive green and white variegated foliage.

* * * * *